(12) United States Patent
Erlichster et al.

(10) Patent No.: US 12,123,865 B2
(45) Date of Patent: Oct. 22, 2024

(54) ASSESSMENT OF BIOMARKER CONCENTRATION IN A FLUID

(71) Applicant: MX3 Diagnostics, Inc., Austin, TX (US)

(72) Inventors: Michael Erlichster, Caulfield North (AU); Efstratios Skafidas, Thornbury (AU); Chathurika Darshani Abeyrathne, Mitcham (AU); Ting Ting Lee, Footscray (AU); Gursharan Chana, Fitzroy North (AU)

(73) Assignee: MX3 Diagnostics, Inc., Austin, TX (US)

( * ) Notice: Subject to any disclaimer, the term of this patent is extended or adjusted under 35 U.S.C. 154(b) by 737 days.

(21) Appl. No.: 17/149,181

(22) Filed: Jan. 14, 2021

(65) Prior Publication Data

US 2021/0215662 A1 Jul. 15, 2021

Related U.S. Application Data

(60) Provisional application No. 62/961,438, filed on Jan. 15, 2020.

(51) Int. Cl.
*G01N 33/487* (2006.01)
*G01N 27/327* (2006.01)
*G01N 27/416* (2006.01)

(52) U.S. Cl.
CPC ......... *G01N 33/487* (2013.01); *G01N 27/327* (2013.01); *G01N 27/4166* (2013.01)

(58) Field of Classification Search
CPC ............ G01N 27/327–3274; C12Q 1/001–005
See application file for complete search history.

(56) References Cited

U.S. PATENT DOCUMENTS

| | | | | |
|---|---|---|---|---|
| 3,947,328 A | * | 3/1976 | Friedenberg | ....... G01N 27/3271 436/95 |
| 3,979,274 A | * | 9/1976 | Newman | ................ C12Q 1/002 435/14 |
| 4,454,007 A | | 6/1984 | Pace | |

(Continued)

FOREIGN PATENT DOCUMENTS

| | | |
|---|---|---|
| CN | 109682878 A | 4/2019 |
| EP | 1710565 A1 | 10/2006 |

(Continued)

OTHER PUBLICATIONS

EPO machine-generated English language translation of WO 2018004191 A1, patent published Jan. 4, 2018 (Year: 2018).*

(Continued)

*Primary Examiner* — Alexander S Noguerola
(74) *Attorney, Agent, or Firm* — Knobbe, Martens, Olson & Bear LLP (57) ABSTRACT

A method and system improving the accuracy and/or interpretability of measurements in a body fluid, such as saliva, sweat or urine involves measurement of multiple parameters in a sample with biosensors. One or more biosensors may reflect the concentration of a target biomarker, and one or more biosensors may describe a parameter of the fluid known to impact the function of the first biosensor the way the measurement of the first biosensor should be interpreted.

8 Claims, 3 Drawing Sheets

(56) References Cited

U.S. PATENT DOCUMENTS

| | | | |
|---|---|---|---|
| 5,222,936 A * | 6/1993 | Stephen | A61N 1/306 604/20 |
| 5,282,950 A * | 2/1994 | Dietze | G01N 27/3273 422/68.1 |
| 5,582,697 A * | 12/1996 | Ikeda | C12Q 1/001 435/817 |
| 5,685,319 A * | 11/1997 | Marett | A61B 5/4266 600/551 |
| 5,714,341 A | 2/1998 | Thieme et al. | |
| 5,776,783 A | 7/1998 | Kell | |
| 5,908,788 A | 6/1999 | Kell | |
| 6,086,748 A | 7/2000 | Durst et al. | |
| 6,102,872 A | 8/2000 | Doneen et al. | |
| 6,315,951 B1 * | 11/2001 | Markart | G01N 21/8483 422/68.1 |
| 6,377,896 B1 * | 4/2002 | Sato | G01N 27/3274 702/23 |
| 6,464,848 B1 * | 10/2002 | Matsumoto | G01N 27/301 204/290.01 |
| 6,554,982 B1 | 4/2003 | Shin et al. | |
| 8,399,259 B2 * | 3/2013 | Fukunaga | G01N 21/255 205/792 |
| 8,465,635 B2 * | 6/2013 | Thurlemann | G01N 33/4905 204/403.01 |
| 9,546,973 B2 | 1/2017 | McIlrath | |
| 9,713,440 B2 * | 7/2017 | Hurd | A61B 5/14532 |
| 10,197,523 B2 | 2/2019 | Huang et al. | |
| 10,258,278 B2 | 4/2019 | Howell et al. | |
| 10,989,724 B1 | 4/2021 | Holmes et al. | |
| 11,219,410 B2 | 1/2022 | Cheuvront | |
| 11,690,566 B2 | 7/2023 | Skafidas et al. | |
| 11,701,036 B2 | 7/2023 | Nguyen et al. | |
| 11,703,436 B2 | 7/2023 | Skafidas et al. | |
| 12,019,045 B2 | 6/2024 | Abeyrathne et al. | |
| 2001/0032785 A1 | 10/2001 | Cha et al. | |
| 2002/0011408 A1 | 1/2002 | Lee et al. | |
| 2002/0060247 A1 | 5/2002 | Krishnaswamy et al. | |
| 2002/0065332 A1 | 5/2002 | Choi et al. | |
| 2003/0150745 A1 | 8/2003 | Teodorczyk et al. | |
| 2003/0159948 A1 | 8/2003 | Benco et al. | |
| 2003/0171697 A1 | 9/2003 | Smith et al. | |
| 2003/0213691 A1 | 11/2003 | Peper et al. | |
| 2004/0173458 A1 * | 9/2004 | Noda | G01N 27/3272 204/452 |
| 2004/0232009 A1 * | 11/2004 | Okuda | G01N 27/3274 205/789 |
| 2004/0238358 A1 | 12/2004 | Forrow et al. | |
| 2005/0023152 A1 * | 2/2005 | Surridge | G01N 27/3272 204/403.1 |
| 2005/0143675 A1 | 6/2005 | Neel et al. | |
| 2005/0201895 A1 | 9/2005 | Donsky | |
| 2005/0279647 A1 | 12/2005 | Beaty | |
| 2006/0137980 A1 | 6/2006 | Lauks et al. | |
| 2007/0015287 A1 | 1/2007 | Robbins et al. | |
| 2007/0048224 A1 | 3/2007 | Howell et al. | |
| 2007/0073127 A1 | 3/2007 | Kiani et al. | |
| 2007/0098600 A1 | 5/2007 | Kayyem | |
| 2007/0272564 A1 | 11/2007 | Huang | |
| 2008/0118397 A1 | 5/2008 | Slowey et al. | |
| 2009/0024060 A1 | 1/2009 | Darrigrand et al. | |
| 2009/0045076 A1 | 2/2009 | Burke et al. | |
| 2009/0173629 A1 | 7/2009 | Kidwell | |
| 2010/0012490 A1 | 1/2010 | Hsu | |
| 2010/0176006 A1 | 7/2010 | Bickford et al. | |
| 2010/0210023 A1 * | 8/2010 | Wong | G01N 33/57407 436/127 |
| 2010/0249652 A1 | 9/2010 | Rush et al. | |
| 2011/0162978 A1 | 7/2011 | Cardosi et al. | |
| 2012/0067741 A1 | 3/2012 | Kranendonk et al. | |
| 2012/0083711 A1 | 4/2012 | Goldstein et al. | |
| 2012/0109011 A1 | 5/2012 | Cogan et al. | |
| 2012/0165626 A1 | 6/2012 | Irina et al. | |
| 2012/0282616 A1 | 11/2012 | Zeijlstra et al. | |
| 2012/0289863 A1 | 11/2012 | Goldstein et al. | |
| 2013/0069120 A1 | 3/2013 | Merz et al. | |
| 2013/0199944 A1 | 8/2013 | Petisee | |
| 2013/0233061 A1 | 9/2013 | Sullivan | |
| 2013/0341186 A1 | 12/2013 | Hsu | |
| 2014/0105788 A1 | 4/2014 | Iwamoto et al. | |
| 2014/0251833 A1 | 9/2014 | Smith et al. | |
| 2014/0277291 A1 | 9/2014 | Pugh et al. | |
| 2014/0297198 A1 | 10/2014 | Wada et al. | |
| 2014/0326037 A1 | 11/2014 | Fukuda et al. | |
| 2015/0091592 A1 | 4/2015 | Elder | |
| 2015/0216471 A1 | 8/2015 | Goldstein et al. | |
| 2015/0217115 A1 | 8/2015 | Avitall | |
| 2015/0226695 A1 | 8/2015 | Bakker et al. | |
| 2015/0226752 A1 | 8/2015 | Nazareth et al. | |
| 2015/0241455 A1 | 8/2015 | Parsons | |
| 2015/0289790 A1 * | 10/2015 | Swenson | A61B 5/14507 600/344 |
| 2015/0359458 A1 | 12/2015 | Erickson et al. | |
| 2016/0011178 A1 | 1/2016 | Hoenes et al. | |
| 2016/0045144 A1 * | 2/2016 | Bansal | A61B 5/14532 600/347 |
| 2016/0120468 A1 | 5/2016 | Mathew et al. | |
| 2016/0266102 A1 | 9/2016 | Knopfmacher | |
| 2016/0320326 A1 | 11/2016 | Zevenbergen et al. | |
| 2016/0361001 A1 | 12/2016 | Tai et al. | |
| 2017/0014822 A1 | 1/2017 | Ker | |
| 2017/0027506 A1 | 2/2017 | Howell et al. | |
| 2017/0067889 A1 | 3/2017 | Tamir | |
| 2017/0138962 A1 | 5/2017 | Southern | |
| 2017/0226557 A1 | 8/2017 | Wang et al. | |
| 2017/0261461 A1 | 9/2017 | Bychkova et al. | |
| 2018/0125400 A1 | 5/2018 | Yang et al. | |
| 2018/0220947 A1 | 8/2018 | Bedell, Jr. | |
| 2019/0150836 A1 | 5/2019 | Skafidas et al. | |
| 2020/0011851 A1 | 1/2020 | Piasio et al. | |
| 2020/0116664 A1 | 4/2020 | Abeyrathne et al. | |
| 2020/0383582 A1 | 12/2020 | Bychkov | |
| 2021/0005233 A1 | 1/2021 | Kim et al. | |
| 2021/0005322 A1 | 1/2021 | Huynh et al. | |
| 2021/0007646 A1 | 1/2021 | Nguyen et al. | |
| 2021/0223239 A1 | 7/2021 | De et al. | |
| 2021/0239586 A1 | 8/2021 | Skafidas et al. | |
| 2022/0013212 A1 | 1/2022 | Tseng et al. | |
| 2022/0122743 A1 | 4/2022 | Erlichster et al. | |
| 2022/0143609 A1 | 5/2022 | Xu et al. | |
| 2024/0122536 A1 | 4/2024 | Skafidas et al. | |
| 2024/0138723 A1 | 5/2024 | Nguyen et al. | |
| 2024/0151623 A1 | 5/2024 | Skafidas et al. | |

FOREIGN PATENT DOCUMENTS

| | | | |
|---|---|---|---|
| EP | 1860432 A1 | 11/2007 | |
| EP | 2075339 A1 | 7/2009 | |
| EP | 2965074 A1 | 1/2016 | |
| JP | 2002-540424 A | 11/2002 | |
| JP | 2003-526108 A | 9/2003 | |
| JP | 4582076 B2 | 11/2010 | |
| JP | 2014-095692 A | 5/2014 | |
| JP | 2014-209095 A | 11/2014 | |
| JP | 2017-532571 A | 11/2017 | |
| KR | 20160035584 A | 3/2016 | |
| KR | 10-2019-0127349 A | 11/2019 | |
| WO | 98/12557 A1 | 3/1998 | |
| WO | 00/58720 A1 | 10/2000 | |
| WO | 01/67079 A1 | 9/2001 | |
| WO | 2007/126920 A1 | 11/2007 | |
| WO | WO2010045247 A1 | 4/2010 | |
| WO | WO2011075711 A1 | 6/2011 | |
| WO | WO 2012012135 A2 * | 1/2012 | C12Q 1/00 |
| WO | WO2014176753 A1 | 11/2014 | |
| WO | 2016/069935 A1 | 5/2016 | |
| WO | WO 2018004191 A1 * | 1/2018 | G01N 27/14 |
| WO | 2018/191322 A1 | 10/2018 | |

OTHER PUBLICATIONS

EPO machine generated English language translation of WO 2013075711 A1, patent published on May 30, 2013 (Year: 2013).*

(56) References Cited

OTHER PUBLICATIONS

"Cepheid and Sherlock Biosciences Establish Collaboration on New GeneXpert Tests for Infectious Diseases and Oncology Leveraging CRISPR Technology, http://cepheid.mediaroom.com/2020-02-28-Cepheid-and-Sherlock-Biosciences-Establish-Collaboration-on-New-GeneXpert-Tests-for-Infectious-Diseases-and-Oncology-Leveraging-CRISPR-Technology, 3 pages (Feb. 28, 2020)."

"Cepheid, Xpert Carba-R, GXCarbar-10, https://www.cepheid.com/Package%20Insert20Files/Xpert-Carba-R-RX-Only-US-IVD-ENGLISH-Package-Insert-301-2438-Rev-F.pdf, Rev. F, 54 pages (Aug. 2019)."

Erlichster et al., "Assessment of Biomarker Concentration in a Fluid," U.S. Appl. No. 62/961,438, filed Jan. 15, 2020, 22 pages.

Erlichster et al., "Pan-Family Assays for Rapid Viral Screening: Reducing Delays in Public Health Responses During Pandemics", Clinical Infectious Diseases, Jul. 20, 2020 (Jul. 20, 2020), pp. 1-6, XP055830068.

Nguyen et al., "Saliva Test Strip and Method" U.S. Appl. No. 62/872,339, filed Jul. 10, 2019, 31 pages.

Paul K et al., "The arrival of a true point-of-care molecular assay-ready for global implementation?", Nov. 1, 2015 (Nov. 1, 2015), pp. e663-e664, XP055830065.

Oncescu et al., "Smartphone based health accessory for colorimetric detection of biomarkers in sweat and saliva," Lab on a Chip 13(16):3232-3238, Jun. 7, 2013.

Skafidas et al., "Biological Fluid Sample Assessment," U.S. Appl. No. 62/967,694, filed Jan. 30, 2020, 21 pages.

Erlichster et al., "Personalized Hydration Assessment and Fluid Replenishment," U.S. Appl. No. 62/876,263, filed Jul. 19, 2019, 30 pages.

Erlichster et al., "Personalized Hydration Assessment and Fluid Replenishment," U.S. Appl. No. 62/957,527, filed Jan. 6, 2020, 35 pages.

A. Moya, et al., "Flexible Microfluidic Bio-Lab-on-a-Chip Multi-Sensor Platform for Electrochemical Measurements", Sensors, 2014 IEEE, pp. 1018-1021 (Year: 2014).

Buhlmann, P. et al., "Carrier-Based Ion-Selective Electrodes and Bulk Opotodes. 2. Ionophores for Potentiometric and Optical Sensors", Chem. Rev., Jun. 1998, vol. 98(4), pp. 1593-1688.

Elmes, R.B.P et al., "Anion recognition by cyclic peptides", Chem. Commun., 2015, vol. 51(24), pp. 4951-4968.

International Preliminary Report on Patentability received for PCT Patent Application No. PCT/US2021/013414, mailed on Jul. 28, 2022, 7 pages.

Joseph, C., et al., "Use of an algorithm applied to urine drug screening to assess adherence to an oxycontin regimen", Journal of Opioid Management, vol. 5, No. 6, Nov. 1, 2009, pp. 359-364.

Nayak, S. et al., "Point-of-Care Diagnostics: Recent Developments in a Connected Age", Analytical Chemistry, 2017, vol. 89 (1), pp. 102-123.

International Search Report and Written Opinion for PCT Application No. PCT/US2021/013414, mailed May 6, 2021, 12 pages.

* cited by examiner

ASSESSMENT OF BIOMARKER CONCENTRATION IN A FLUID

CROSS-REFERENCE TO RELATED APPLICATIONS

This application claims the benefit of U.S. Provisional Patent Application No. 62/961,438, filed Jan. 15, 2020, entitled, "ASSESSMENT OF BIOMARKER CONCENTRATION IN A FLUID." The disclosure of this priority application is hereby incorporated by reference in its entirety into the present application.

TECHNICAL FIELD

This application describes biomedical systems and methods. More specifically, the application describes a method and system for determining and interpreting the concentration of a compound in a human or animal subject using biosensors.

BACKGROUND

Point-of-care testing systems allow for measurement of biomarkers (e.g., metabolites, hormones, electrolytes) in biological samples outside of a laboratory, such as in a clinic or personal residence. By reducing labor and transport costs, point-of-care testing is an attractive alternative to laboratory testing, especially for frequent and/or routine tests.

Most existing point-of-care tests use blood as the sample. This is due to the established value of blood parameters in conventional laboratory analysis, as well as the tight physiological regulation of blood parameters such as pH (7.35-7.45) and osmolarity (275-300 milliosmoles (mOSM)). It is challenging, however, for most people to collect sufficient amounts of blood by themselves at home to be able to measure biomarkers. Therefore, it would be desirable to develop alternative point-of-care testing systems that use an alternative bodily fluid that can be collected less invasively, such as saliva, as the sample fluid.

Saliva is a rich source of biomarkers that can be used to monitor health and wellness, including hormones, metabolites, nucleic acids and drugs. One challenge of analyzing saliva is that it can have markedly varying properties between individuals, as well as within the same individual over time. One highly variable parameter in saliva is salivary acidity/alkalinity (pH). Saliva pH can vary between pH 6 and pH 8, depending on many factors, such as diet, age and oral health. Another bodily fluid commonly used for biomarker assessment is urine. As with saliva, urinary pH can vary dramatically for pH 4.5 to pH 8 depending on diet and health status.

Many compounds and reactions typically used in point-of-care biosensor chemistry are sensitive to pH. One such compound is an enzyme, a biological molecule that increases the rate of a chemical reaction. A specific enzyme from a specific species will have a pH optimum outside of which enzyme activity is reduced. As an illustrative example, the enzyme D-3-Hydroxybutyrate dehydrogenase (HBD), derived from the bacterium *Pseudomonas* sp., has a pH optimum of approximately 8.5. At pH 7, approximately 80% of relative activity is observed, and at pH 6, approximately 20% of relative activity is observed. As such, without correction for pH, the output of an enzymatic biosensor may be dramatically misinterpreted. To a lesser degree, immunosensors, biosensors that rely on the binding of an antibody and an antigen, are also impacted by pH. While there is typically a broader functional range (e.g. pH 6.5-pH 8.5), outside of this range binding strength is reduced.

Another highly variable parameter in saliva is salivary osmolarity. Salivary osmolarity can vary from 20 mOSM to 300 mOSM, depending on the genetic makeup, diet and hydration status of the individual being measured. Similarly, urinary osmolarity can vary dramatically from 100 to 1000 mOSM, depending on hydration status, diet and activity of the individual being measured. Sweat osmolarity is also highly variable and can vary between 50 and 300 mOSM, depending on an individual's genetic makeup, diet, level of activity and environmental acclimation.

Similarly, the osmolarity of a fluid can impact the output of a biosensor. As an illustrative example, an electrochemical impedance spectroscopy immunosensor uses the concentration-dependent changes in impedance due to the binding of a biomarker to assess concentration. As the osmolarity of the sample would greatly impact the impedance measurement, one or more wash steps are used to regulate the osmolarity of the sample. Where such wash steps are not practical, without correction for osmolarity, the output of an impedimetric biosensor may be dramatically misinterpreted.

As an additional application of osmolarity, many biomarkers in saliva, sweat or urine are derived from blood through passive diffusion or active transport. As such, hydration status and body water content may impact the availability of biomarkers in these fluids. Knowledge of the osmolarity of these fluids, to assist in assessment of hydration status, may allow for improved interpretation of biomarker concentration.

Existing point-of-care enzymatic biosensors and immunosensors developed for blood analysis do not account for pH or osmolarity. Therefore, it would be desirable to have a biosensor that could correct for pH and/or osmolarity effects on test strip function, as well as the effect of osmolarity on biomarker availability. This test strip would improve the accuracy of biosensors on fluids where parameters are less regulated and improve the value of non-invasive fluid measurement for prediction of established blood parameters. Ideally, such a method would be relatively easy to employ and cost effective, to make it accessible to many users. This application addresses at least some of these objectives.

SUMMARY

The assignee of the present application has filed previous patent applications describing systems, methods and devices for testing, measuring and analyzing saliva, to measure a subject's hydration level, as well as for measuring other substances (e.g., sweat) and/or physiological parameters in a human or animal subject. These previous patent applications include U.S. patent application Ser. No. 16/197,530 (U.S. Pub No. 2019/0150836), titled "Saliva Testing System," filed Nov. 21, 2018; Ser. No. 16/598,000, titled "Ion Selective Sensor," filed Oct. 10, 2019; 62/869,210 titled "Biological Fluid Analysis System," filed Jul. 1, 2019; 62/872,339 titled "Saliva Test Strip and Method," filed Jul. 10, 2019; 62/876,263 titled, "Personalized Hydration Assessment and Fluid Replenishment," filed Jul. 19, 2019; and 62/957,527 titled, "Personalized Hydration Assessment and Fluid Replenishment," filed Jan. 6, 2020. All of the above-referenced patent applications are hereby incorporated by reference into the present application, and they are referred to below as "the Incorporated Applications."

The present application adds to the technologies in the Incorporated Applications by describing a system and method for improving the accuracy of measurements in body fluids through correction of known chemical effects on the output of biosensors. This application also describes a method of using chemical parameters which are known to impact the way a measurement should be interpreted against a reference method to improve the utility of measurement data from bodily fluids.

In one aspect of the present disclosure, a system for measuring a concentration of a biomarker in a body fluid includes: a first biosensor configured to generate a first output proportional to the concentration of the biomarker in the body fluid; a second biosensor configured to measure a pH of the body fluid and provide the measured pH as a second output; a reference dataset describing an impact of the second output on the first output; and a processor configured to apply the reference dataset to the first output and the second output to provide a corrected biomarker concentration.

The first biosensor and the second biosensor are located on a single test strip or on two separate test strips. In some examples, the first biosensor is located on a first test strip, the second biosensor is located on a second test strip, and the first test strip and the second test strip are configured to be applied to an analysis device either in sequence or in parallel. In other examples, the first biosensor is located on a first test strip configured to be applied to a first analysis device, and the second biosensor is located on a second test strip configured to be applied to a second analysis device. In other embodiments, three or four or more measurements may be taken, using one, two or more test strips. For example, in one example uric acid in saliva may be measured at the same time that pH and osmolarity of the saliva sample is measured.

In various examples, the first biosensor and the second biosensor contain one or more enzymes, antibodies or any other molecule that is used for detection. In some examples, the system may also include an additional sensor located on a test strip or an analysis device, configured to measure a temperature. In such an embodiment, the processor is further configured to use the measured temperature in providing the corrected biomarker concentration.

In some examples, the first biosensor and/or the second biosensor is configured for a single use and is disposable after the single use. Alternatively, the first biosensor and/or the second biosensor may be reusable for multiple measurements. In some examples, the system is configured to provide the measured pH of the second output to a user.

In another aspect of the present disclosure, a system for measuring the concentration of a biomarker in a body fluid includes: a first biosensor configured to generate a first output proportional to the concentration of the biomarker in the body fluid; a second biosensor configured to measure an osmolarity of the body fluid and provide the measured osmolarity as a second output; a reference dataset describing an impact of the second output on the first output; and a processor configured to apply the reference dataset to the first output and the second output to provide a corrected biomarker concentration. In some examples, the system is configured to provide the measured osmolarity of the second output to a user.

In another aspect of the disclosure, a system for measuring the concentration of a biomarker in a body fluid includes: a first biosensor configured to generate a first output proportional to the concentration of the biomarker in the body fluid; a second biosensor configured to measure a pH of the body fluid and provide the measured pH as a second output; a third biosensor configured to measure an osmolarity of the body fluid and provide the measured osmolarity as a second output; a reference dataset describing an impact of the second output and the third output on the first output; and a processor configured to apply the reference dataset to the first output, the second output and the third output to provide a corrected biomarker concentration.

In some examples, the first biosensor, the second biosensor and the third biosensor are located on a single test strip. In other examples, the first biosensor, the second biosensor and the third biosensor are all located on separate test strips and are configured to be applied to an analysis device in sequence or in parallel. In other examples, the first biosensor, the second biosensor and the third biosensor are all located on separate test strips and are configured to be applied to three different analysis devices. The first biosensor, the second biosensor and the third biosensor may contain one or more enzymes or antibodies. In various examples, the system is configured to provide the measured pH of the second output and/or the measured osmolarity of the third output to a user.

In another aspect of the present disclosure, a system of measuring the concentration of multiple biomarkers in a body fluid includes: multiple biosensors, each having an output that is proportional to a concentration of a different one of the multiple biomarkers in the body fluid; at least one additional biosensor configured to measure a pH of the body fluid and/or an osmolarity of the body fluid; a reference dataset describing an impact of the measured pH and/or the measured osmolarity on the output of each of the multiple biosensors; and a processor configured to apply the reference dataset to the output of all of the multiple biosensors to provide a corrected biomarker concentration.

In another aspect of the present disclosure, a system for interpreting the concentration of a biomarker in a body fluid includes: a first biosensor configured to generate a first output proportional to the concentration of the biomarker in the body fluid; a second biosensor configured to measure an osmolarity of the body fluid and provide the measured osmolarity as a second output; a reference dataset describing an impact of the second output on the first output on the availability of the biomarker in the body fluid; and a processor configured to apply the reference dataset to the first output and the second output to provide a corrected biomarker concentration.

In another aspect of the present disclosure, a method for measuring a concentration of a biomarker in a body fluid involves: generating a first output with a first biosensor, where the first output is proportional to the concentration of the biomarker in the body fluid; measuring at least one of a pH or an osmolarity of the body fluid with a second biosensor and providing the at least one of the pH or the osmolarity as a second output; generating a reference dataset describing an impact of the second output on the first output; and using a processor to apply the reference dataset to the first output and the second output to provide a corrected biomarker concentration.

In some examples, the first biosensor and the second biosensor are located on a single test strip, and the method further involves coupling the single test strip with an analysis device that includes the processor. Alternatively, the first biosensor may be located on a first test strip, and the second biosensor may be located on a second test strip, where the method further involves coupling the first test strip and the second test strip with an analysis device that includes the processor. In yet another example, the first biosensor is located on a first test strip configured to be applied to a first analysis device, the second biosensor is located on a second test strip configured to be applied to a second analysis device, and the method further involves coupling the first test strip with the first analysis device and coupling the second test strip with the second analysis device.

In various examples, the first biosensor and the second biosensor contain one or more enzymes or antibodies. In some embodiments, the method also includes using an additional sensor located a test strip or an analysis device to measure a temperature, and using the measured temperature in providing the corrected biomarker concentration. In some examples, the method may involve providing the measured pH and/or the measured osmolarity of the second output to a user.

These and other aspects and embodiments are described in greater detail below, in relation to the attached drawing figures.

DETAILED DESCRIPTION

The present application describes various embodiments and features of a system and method for determining the concentration of a biomarker in a body fluid. Although the following disclosure focuses on the analysis of sweat, saliva and/or urine, the embodiments described below, or variations of those embodiments, may be used for analysis of any other bodily fluid, such as blood.

The Test System

Figure 1:
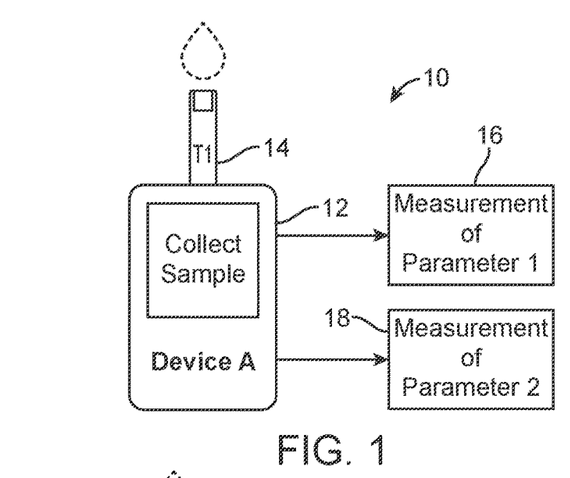
FIG. 1 shows a system in which one sample is used to determine multiple parameters with a single test strip, according to one embodiment.
Figure 2:
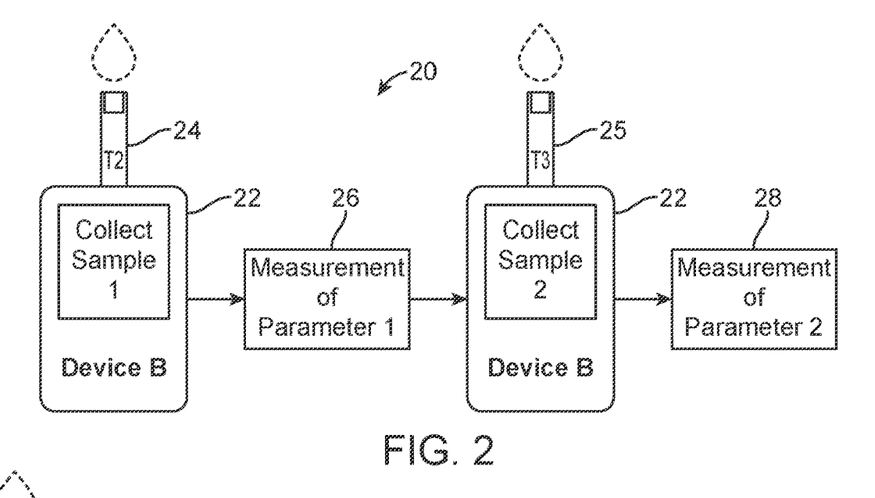
FIG. 2 shows a system in which multiple test strips are used in sequence with a single meter to measure multiple parameters in separate samples, according to an alternative embodiment.
Figure 3:
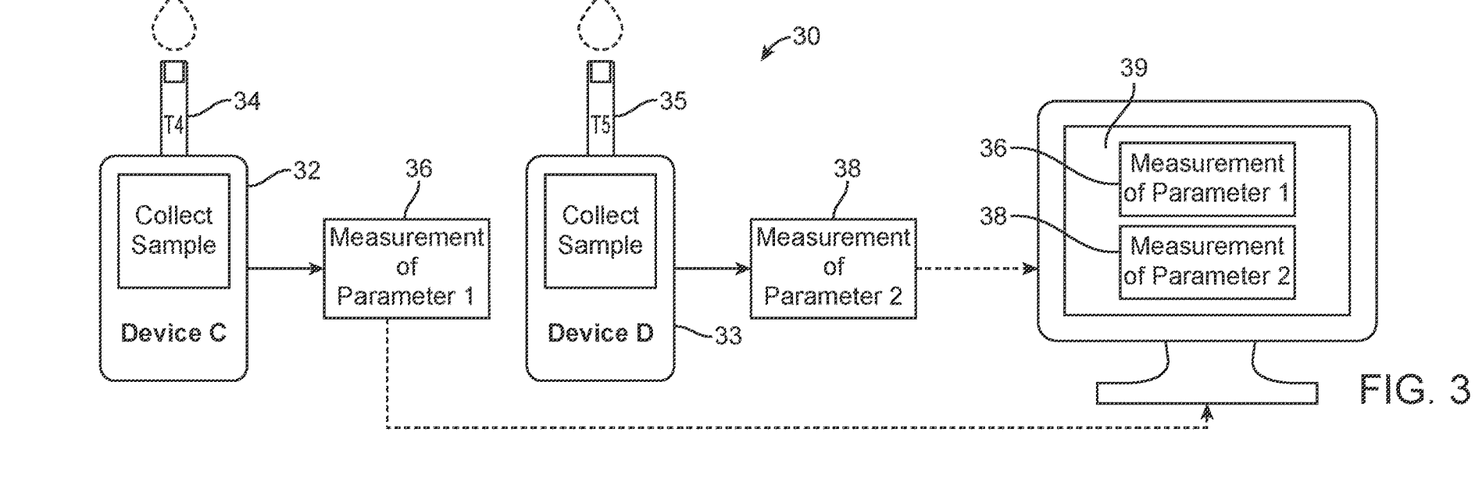
FIG. 3 shows a system in which multiple test systems and test strips are used to communicate with a central repository, according to another alternative embodiment.

FIGS. 1-3 illustrate multiple embodiments of a test system for measuring multiple parameters in a body fluid. These parameters may include, but are not limited to, the concentration of a metabolite, hormone, electrolyte or narcotic in the body fluid, the acidity of the body fluid, and/or the osmolarity of the body fluid. Parameters are measured using biosensors, which may apply electrochemical (e.g., amperiometric, voltametric, impediometric), optical or other techniques.

FIG. 1 is a diagrammatic illustration of a body fluid test system 10 according to one embodiment. In this embodiment, the test system 10 includes a handheld body fluid measurement device 12, which is used with one test strip 14 (at a time) that tests one body fluid sample, such as saliva. The test system 10 is used to determine multiple parameters 16, 18 with the single test strip 14 that holds the single sample. Additional samples, from the same or different subjects, may be tested using additional test strips sequentially on the handheld device 12.

FIG. 2 is a diagrammatic illustration of an alternative embodiment of a body fluid test system 20, which also includes a handheld body fluid measurement device 22. In this embodiment, a first test strip 24 is used to collect a first sample, and the handheld device 22 measures a first parameter 26 from the first sample. Then, the first test strip 24 is removed, a second test strip 25 is used to collect a second sample, and the handheld device 22 is used to measure a second parameter 28 from the second sample. Thus, this embodiment of the test system 20 is used to sequentially test multiple parameters of a body fluid of a subject.

FIG. 3 shows is a diagrammatic illustration of another alternative embodiment of a body fluid test system 30. In this embodiment, a first handheld body fluid measurement device 32 is used with a first test strip 34 and a first body fluid sample to measure a first parameter 36. A second handheld body fluid measurement device 33 is also used with a second test strip 35 and a second body fluid sample to measure a second parameter 38. The measurement data from the measured parameters 36, 38 are then transmitted, for example wirelessly, from the handheld measurement devices 32, 33 to a central repository 39, for example a computer processor, a database, or the like. The parameters may be sent automatically or may be manually recorded in the central repository, according to various embodiments.

Biosensors (referred to also as "test strips" herein) may be single-use or reusable, the latter being designed to be cleaned between use. Tests strips may be used to collect a sample directly from a human or animal subject, such as by placing a free end of a test strip on the tongue or in the mouth. Alternatively, the test strip may be used to collect a sample from a collection receptacle. Test strips may also be embedded in a patch or clothing to allow for collection of a sample as it is generated by the body (e.g., a sweat patch applied to skin).

Additional parameters, not related to the body fluid composition, may also be recorded by the test system. These parameters may include, but are not limited to, ambient temperature, humidity, wind-speed, elevation, self-rated exertion or heart rate. Parameters may be automatically measured through integrated sensors, imported from external databases or manually input by the user.

The Reference Dataset—Correction

The reference dataset is a previously-established dataset describing the impact of one or more parameters, such as pH and/or osmolarity, on the output of a biosensor. The reference dataset may also describe the impact of additional parameters, such as environmental parameters, on biosensor performance or result interpretation. The reference dataset may be universal, specific to a population or specific to an individual.

Figure 4A:
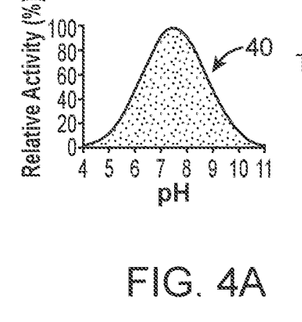
FIG. 4A is a graph illustrating the impact of sample pH on the output of an enzyme-based amperometric sensor, according to one embodiment.

FIG. 4A is a graph showing an illustrative example of the impact of sample pH on the output of an enzyme-based amperometric sensor. In this example, a curve 40 is observed, in which pH below 5 or greater than 10 reduces the output by over 95%, a pH of 6 or 9 reduces the output by 50%, and pH of 7 to 8 provides an output above 90%, with a maximum observed at pH 7.5.

Figure 4B:
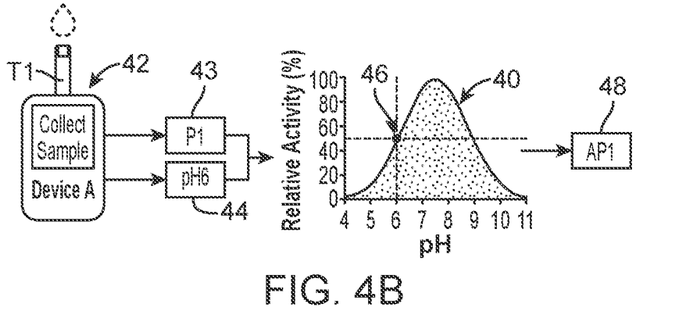
FIGS. 4B and 4C illustrate a method for using the curve of FIG. 4A to correct the raw output of a biosensor, according to one embodiment.

FIGS. 4B and 4C illustrate a method for using the curve from FIG. 4A to correct the raw output of a biosensor 42, whereby the same raw output is corrected to two different results, based on the sample pH. In a first example, referring to FIG. 4B, a first sample is measured with the biosensor 42 to give a first parameter measurement 43 and is shown to have a pH measurement 44 of pH 6. According to the curve 40, the measured pH 6 means that the output of the biosensor 42 is approximately 50% of the maximum output, as illustrated by the point 46 on the curve 40. To adjust for this lower-than-maximum output, the first parameter measurement 43 is multiplied by a multiplier, in this case is 2, to arrive at an adjusted parameter measurement 48.

Figure 4C:
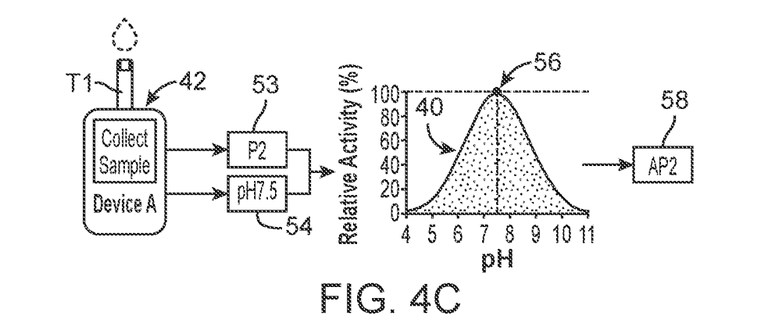

Referring to FIG. 4C, a second parameter measurement adjustment is illustrated. Here, the biosensor 42 produces a second parameter measurement 53 with a pH measurement 54 of pH 7.5. At that pH, the biosensor output is at approximately 100% of the maximum output, as illustrated by the point 56 on the curve 40. The adjusted output is thus multiplied by 1 for the measured pH effect, to arrive at an adjusted parameter measurement 58.

Figure 5A:
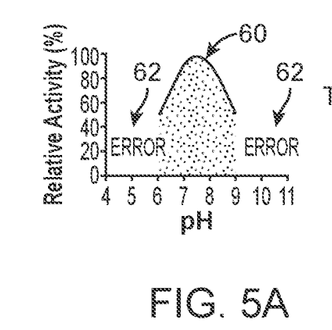
FIG. 5A is a graph illustrating how pH may be used to define an allowable range of measurements, according to one embodiment.
Figure 5B:
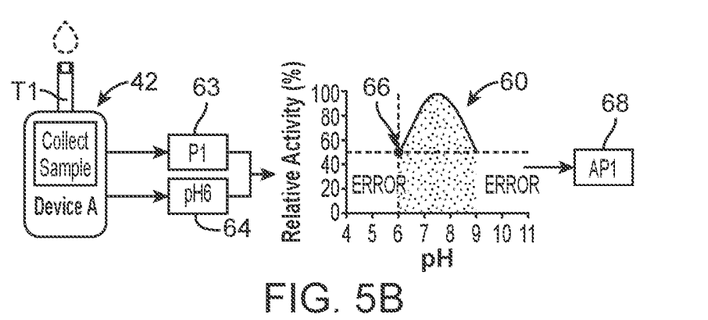
FIGS. 5B and 5C illustrate a method for using the curve of FIG. 5A to correct the raw output of a biosensor (FIG. 5B) and exclude a measurement as an error due to the pH of the sample being outside of the allowable range (FIG. 5C), according to one embodiment.
Figure 5C:
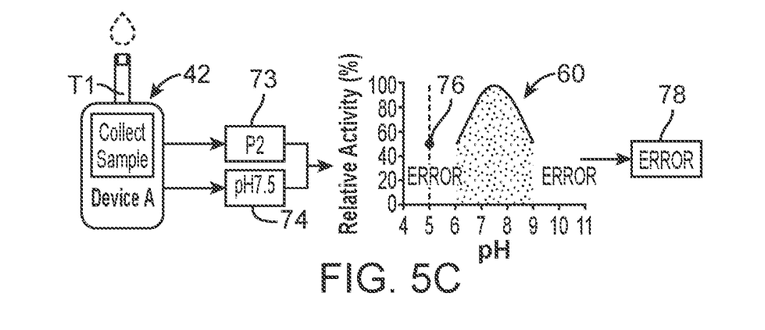

Referring now to FIGS. 5A-5C, another example of a parameter measurement adjustment method is illustrated. Referring first to FIG. 5A, in this embodiment, a curve 60 indicates activity levels of the biosensor 42 between pH 6 and pH 9. In this example, a measured pH<6 or measured pH>9 is shown to completely prevent (or unpredictably prevent) the function of the biosensor 42, so a measured pH in those ranges (pH<6 or >9) indicates an error 62. In such an instance, an error message may be indicated on the biosensor 42, to indicate to the user that an accurate measurement could not be made from that sample. If the measured pH is in the range of 6-9, the curve 60 may be applied as in the previous examples, to adjust the measured parameter data.

Referring to FIG. 5B, for example, the biosensor 42 is used to measure a sample to provide a first parameter measurement 63 and a pH measurement 64 of pH 6. The pH 6 suggests that the biosensor output is 50% of the maximum, as illustrated by the point 66 on the curve 60. The method thus involves doubling the measured parameter 63, to adjust for the pH 6 and arrive at the adjusted parameter measurement 68.

Referring to FIG. 5C, in another example, the biosensor 42 is used to measure a sample resulting in a second parameter measurement 73 and showing a pH measurement 74 of pH 7.5. As illustrated by the point 76, this pH suggests that the biosensor output is unreliable. An error message 78 is then presented on the biosensor 42.

The Reference Dataset—Interpretation

The reference dataset may also describe the impact of one or more parameters on the relationship between the concentration of a biomarker in blood and the concentration of a biomarker in the body fluid being measured. This estimated blood concentration may have additional value beyond the saliva concentration, as normal blood ranges and the uses of this blood parameter may have been established elsewhere. In other words, the saliva measurement can be used to inform the value of a metabolite of blood. For example, salivary uric acid level may be measured, and this measurement may be used to estimate the level of uric acid in blood. The estimated blood value of uric acid may then be compared to established reference levels, and a treatment may be determined based on the comparison.

Figure 6A:
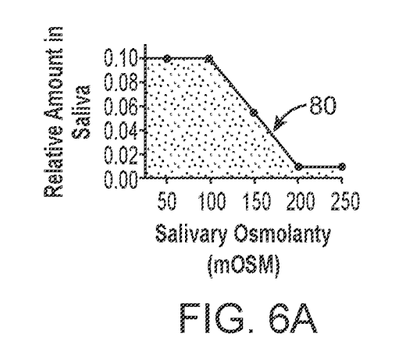
FIGS. 6A-6C illustrate a method for using a parameter to assist in the interpretation of a sample concentration, according to one embodiment.
Figure 6B:
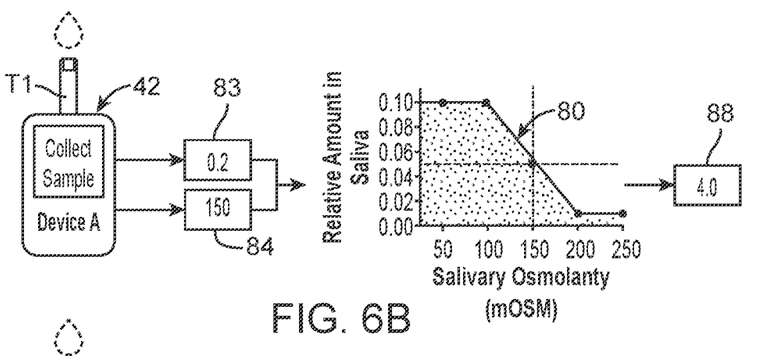
Figure 6C:
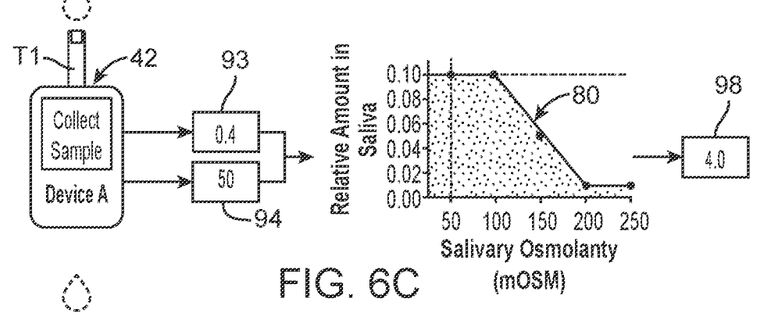

Referring now to FIGS. 6A-6C, a method is illustrated for using a parameter to assist in the interpretation of a sample concentration. FIG. 6A shows an illustrative example of a curve 80 demonstrating the relationship between salivary osmolarity and relative metabolite concentration in saliva and blood. At salivary osmolarity>200, very little metabolite is observed in saliva, resulting in a very large ratio of 1:100 between saliva and blood. At salivary osmolarity of 150, a ratio of 1:20 is observed. At osmolarity<100, a ratio of 1:10 is observed.

FIGS. 6B and 6C show the use of the curve 80 to correct the estimated blood concentration of this analyte, based on the saliva concentration, whereby two different raw outputs are interpreted differently, due to the sample osmolarity. In this example, the osmolarity of a sample is used to assist in the interpretation of the biosensor output. In FIG. 6B, the biosensor 42 is used to measure a saliva sample, producing an osmolarity measurement 84 (150 mOsm) and a metabolite concentration 83 (0.2 mmol). At this osmolarity, a ratio of 1:20 between saliva and blood has been established, and a predicted blood concentration 88 (4.0 mmol) is presented to the user.

In FIG. 6C, a second sample from this user is measured with an osmolarity measurement 94 (50 mOsm) and a metabolite concentration 93 (0.4 mmol). At this osmolarity, a ratio of 1:10 between saliva and blood has been established, and a predicted blood concentration 98 (4.0 mmol) is presented to the user. Despite different salivary concentrations being observed for these two measurements, the predicted blood concentrations are the same.

Figure 7A:
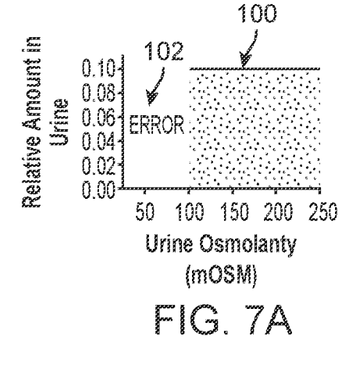
FIGS. 7A and 7B illustrate a method for using a parameter to predict errors for a sample measurement, according to one embodiment.
Figure 7B:
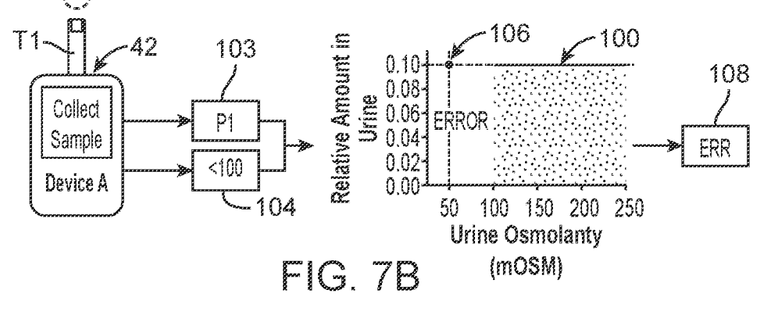

Referring to FIGS. 7A and 7B, in another embodiment, the osmolarity of a sample is used to flag an error. FIG. 7A shows a representative curve 100 of the way a parameter, urine osmolarity, may be used to define an allowable range. Any reading outside of the curve 100 results in an error message 102.

FIG. 7B shows the use of the curve 100 to exclude a measurement as an error due to the osmolarity of the sample being outside of the allowable range. In this example, a first parameter measurement 103 and an osmolarity measurement 104 of a urine sample are provided from the biosensor 42. Since the osmolarity measurement 104 is less than 100, this represents an unpredictable urine sample, as illustrated by the point 106, which prevents the use of this parameter in urine to predict a blood concentration. An error message 108 is presented on the biosensor 42, to warn the user that an accurate prediction of the blood concentration could not be made with this sample.

Although the foregoing is believed to be a complete and accurate description of various examples and features of the invention, alternations may be made to any given embodiment, without departing from the scope of the invention. Any embodiments or features described above may be added to or combined with other embodiments described herein.

We claim:

1. A system for measuring the concentration of a biomarker in a body fluid, the system comprising:
   a first biosensor configured to generate a first output proportional to the concentration of the biomarker in the body fluid;
   a second biosensor configured to measure an osmolarity of the body fluid and provide the measured osmolarity as a second output;
   a reference dataset describing an impact of the second output on the first output; and a processor configured to apply the reference dataset to the first output and the second output to provide a corrected biomarker concentration, wherein the body fluid is saliva.

2. The system of claim 1, wherein the system is configured to provide the measured osmolarity of the second output to a user.

3. A system for measuring the concentration of a biomarker in a body fluid, the system comprising:
   a first biosensor configured to generate a first output proportional to the concentration of the biomarker in the body fluid;
   a second biosensor configured to measure a pH of the body fluid and provide the measured pH as a second output;
   a third biosensor configured to measure an osmolarity of the body fluid and provide the measured osmolarity as a third output;
   a reference dataset describing an impact of the second output and the third output on the first output; and
   a processor configured to apply the reference dataset to the first output, the second output and the third output to provide a corrected biomarker concentration.

4. The system of claim 3, wherein the first biosensor, the second biosensor and the third biosensor are located on a single test strip.

5. The system of claim 3, wherein the first biosensor, the second biosensor and the third biosensor are all located on separate test strips and are configured to be applied to an analysis device in sequence.

6. The system of claim 3, wherein the first biosensor, the second biosensor and the third biosensor are all located on separate test strips and are configured to be applied to an analysis device in parallel.

7. The system of claim 3, wherein the first biosensor, the second biosensor and the third biosensor are all located on separate test strips and are configured to be applied to three different analysis devices.

8. The system of claim 3, wherein the system is configured to provide at least one of the measured pH of the second output or the measured osmolarity of the third output to a user.

* * * * *